United States Patent [19]

Lisowsky

[11] Patent Number: 5,618,956
[45] Date of Patent: Apr. 8, 1997

[54] ASYMMETRICALLY SUBSTITUTED METALLOCENES WHICH ARE FUNCTIONALIZED ON ONE CYCLOPENTADIENYL RING, AND THEIR PREPARATION

[75] Inventor: Richard Lisowsky, Kamen, Germany

[73] Assignee: Witco GmbH, Bergkamen, Germany

[21] Appl. No.: 685,994

[22] Filed: Jul. 25, 1996

[30] Foreign Application Priority Data

Aug. 30, 1995 [EP] European Pat. Off. ............. 95113595

[51] Int. Cl.$^6$ .................. C07F 7/08; C07F 7/16; C07F 17/00
[52] U.S. Cl. ........................................ 556/12
[58] Field of Search ........................ 556/11, 12

[56] References Cited

U.S. PATENT DOCUMENTS 5,103,030  7/1992  Rohrmann et al. .

FOREIGN PATENT DOCUMENTS

0530908A1  3/1993  European Pat. Off. .

OTHER PUBLICATIONS

Churakov, Andrew V., "Synthesis of sandwich and half-sandwich complexes of Ti, Zr and Hf containing $\eta^5$-$C_5H_4SiMe_2Cl$ ligand", *Journal of Organometallic Chemistry*, 1995 pp. C81–C83.

Renault, P. "Chlorures de mono-et dialkyl-zirconocene et-hafnocene", *Journal of Organometallic Chemistry*, 1978 pp. 35–42.

Renaut, P. "Cyclopentadienylhafnium trichloride, its synthesis and use to prepare a chiral hafnium compound", *Jouranl of Organometallic Chemistry*, 1977 pp. C35–C36.

Schore, Neil E. "Synthesis of $(C_6H_5)_2PCH_2Si(CH_3)_2$ $C_5H_4Li$", *Journal of the American Chemical Society*, 1979, pp. 7410–7412.

Spaleck, Von W. "Hochmolekulares polypropylen durch maßgescheniderte Zirconocenkatalysatoren", *Angrew. Chem.*, 1992, pp. 1373–1376.

Sinn, Von H. "Lebende polymere bei Ziegler–katalysatoren extremer produktivitat", *Angrew. Chem.*, 1980, pp. 396–402.

Wolfgang, Von A. "Erstes Beispiel eines ethyleneselektiven löslichen Ziegler–Katalysators der Zirconocen–Klasse" *Angrew. Chem.*, 1989, pp. 1536–1538.

*Primary Examiner*—Gary Geist
*Assistant Examiner*—Jean F. Vollano
*Attorney, Agent, or Firm*—Scully, Scott, Murphy & Presser

[57] ABSTRACT

The invention relates to compounds of the general formula (1)

$$(R^1R^2X^1Si((R^3)_aCp))((R^4)_aCp)M(X^2)_n \qquad (1)$$

in which $R^1$ and $R^2$=independently of one another an alkyl or aryl radical, $X^1$=F, Cl, Br, I, p-tolyl$SO_3$—, $F_3CSO_3$—, $F_3CCO_2$— or $H_3CCO_2$—, $R^3$ and $R^4$=identical or different alkyl, alkyl ether, aryl or aryl ether groups where $0 \leq a \leq 4$, Cp=a cyclopentadienyl, indenyl, tetrahydroindenyl or fluorenyl radical, M=a transition metal from groups 3–6 (IUPAC notation), in particular Ti, Zr or Hf, $X^2$=F, Cl, Br or I, the oxidation number of the transition metal minus 2.

Also disclosed is a process of making compounds of formula (1) by reacting the metallocene counterpart thereof with acid $HX^1$.

8 Claims, No Drawings

ASYMMETRICALLY SUBSTITUTED METALLOCENES WHICH ARE FUNCTIONALIZED ON ONE CYCLOPENTADIENYL RING, AND THEIR PREPARATION

FIELD OF THE INVENTION

The invention relates to novel asymmetrically substituted metallocenes which are functionalized on one cyclopentadienyl ring, and to a process for their preparation.

BACKGROUND OF THE INVENTION

With the knowledge that metallocenes are starting components which give highly active polymerization catalysts in combination with specific activators, such as, for example, aluminoxanes, the synthesis of such compounds is also continuously increasing in importance (Angewandte Chemie 1980, Int. 92, 396; Angewandte Chemie 1992, 104, 1373; Angewandte Chemie 1989, 101, 1536).

Although general synthetic methods for the preparation of metallocenes have been described in the literature, these cannot be used in all cases. For example, asymmetrical metallocenes, i.e. those carrying two differently substituted cyclopentadienyl rings, can only be prepared with difficulty by metallation of cyclopentadienyl derivatives followed by reaction with a transition-metal halide, as shown in equation I:

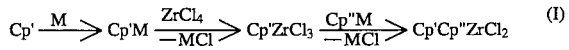

(I)

M=metallating agent (Li, Na); Cp' and Cp"=cyclopentadienyl radical.

Compounds Cp'Cp"ZrCl$_2$ can, with limitations, be obtained, for example, by the synthesis shown diagrammatically in equation I by reacting ZrCl$_4$ with Cp'M, isolation of Cp'ZrCl$_3$ followed by reaction with Cp"M.

Owing to low yields and difficulties in purification, the synthesis of, in particular, Cp'ZrCl$_3$ is difficult (J. Am. Chem. Soc., 1979, 101, 7410; J. Am. Chem. Soc. 1978, 148, 35–42; J. Organometal. Chem., 1977, 127, C35).

However, this synthetic route fails if one of the cyclopentadienyl systems also carries a functional group which is capable of reacting with the metallating agent M, for example in the case of compounds

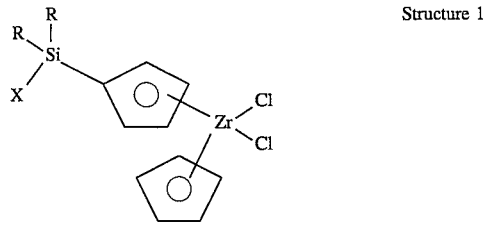

Structure 1

For example, compounds of the (R$_2$SiX)Cp'ZrCp"Cl$_2$ (Structure 1) where X =Cl, Br or I have, owing to the reactivity of the X-Si bond toward metallating agents, until now only been synthesized in individual cases (J. Organometal. Chem. 1995, 489, C81) and not at all for the cyclopentadienyl group (such as an indenyl or tetrahydroindenyl radical).

One object of the present invention is therefore to provide novel asymmetrically substituted metallocenes, i.e. those which are functionalized on only one cyclopentadienyl ring (Cp ring).

BRIEF SUMMARY OF THE INVENTION

This object is achieved by a process for the preparation of these novel Cp compounds which is characterized in that the starting compounds are cleaved selectively at the Si-Cp bond by means of acids in an inert solvent, if necessary at elevated temperature.

The invention relates to asymmetrical substituted compounds of the general formula (1) and to a process for their preparation thereof:

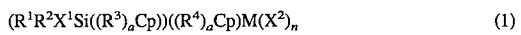

in which

R$^1$ and R$^2$=independently of one another the same or different and each is an alkyl radical containing 1 to 7 carbon atoms or an aryl radical containing up to 7 carbon atoms, X$^1$=F, Cl, Br, I, p-tolylSO$_3$—, F$_3$CSO$_3$—, F$_3$CCO$_2$— or H$_3$CCO$_2$—, R$^3$ and R$^4$=independently of one another the same or different and each is an alkyl or alkyl ether group containing 1 to 9 carbon atoms, or an aryl or aryl ether group containing up to 9 carbon atoms, and 0≦a≦4, Cp=a cyclopentadienyl, indenyl, tetrahydroindenyl or fluorenyl radical, M=a transition metal from groups 3–6 (IUPAC notation), in particular Ti, Zr or Hf, X$^2$=F, Cl, Br or I, n=the oxidation number of the transition metal minus 2, characterized in that a compound of the general formula (2)

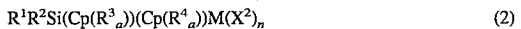

where R$^1$, R$^2$, Cp, R$^3$, R$^4$, a, M, X$^2$ and n are as defined above, is reacted with an inorganic or organic acid HX$^1$ in an inert solvent, if necessary at elevated temperature, with selective cleavage of the Cp-Si bond, as shown in the general equation II

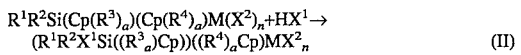

DETAILED DESCRIPTION OF THE INVENTION

The compounds of the general formula (2) which can be used in accordance with the invention can be prepared by processes known per se—as described, for example, in U.S. Pat. No. 5,103,030, EP-A-0 530 908 and EP-A-0 669 340. The compounds where Z=Si, which can be prepared as described in EP-A-0 669 340, claim 1, are preferred in accordance with the invention.

Suitable solvents in accordance with the invention are all aprotic, organic solvents in which the compounds are at least partially soluble, and mixtures thereof. The amount of solvent is unimportant and can be matched to the particular solubility of the starting material, it not being necessary for all the product to be dissolved, but can in part also be in the form of a dispersion. For technical reasons, the amount of solvent should be selected so that a stirrable mixture is present and sufficient starting material is in solution for reaction with the acid HX$^1$.

Particularly suitable solvents are aromatic solvents such as toluene and xylene, halogenated hydrocarbons such as methylene chloride or chloroform, and ethers such as diethyl ether or tetrahydrofuran.

In the process, the corresponding metallocene of the formula (2) is introduced at room temperature into a solvent or solvent mixture and mixed with the acid $HX^1$, and the mixture is stirred until conversion is complete.

Suitable acids $HX^1$ which can be used are inorganic and organic acids. Preference is given to monobasic acids, such as p-toluenesulfonic acid, trifluoromethylsulfonic acid, trifluoroacetic acid, acetic acid and in particular inorganic acids, such as HF, HCl, HBr, HI or mixtures thereof. At least one mol of the monobasic acid is employed per mol of Si-Cp bond to be cleaved.

If necessary, the mixture can also be warmed in order to increase the reaction rate.

The temperature depends on the optimum required for cleavage of the Si-Cp bond and is generally from 20° to 150° C., depending on the reactants.

In the case of readily volatile reagents $HX^1$, the starting material can be prevented from escaping via the gas phase by carrying out the reaction in a sealed vessel at pressures from 1 to 150 bar ($10^3$ hPa–$1.5 \times 10^5$ hPa).

In the case of metallocenes which, owing to their substitution on the Cp ligand, can exist in stereoisomeric forms [racemate (rac) and meso compounds (meso)], both mixtures of rac:meso compound and the respective pure stereoisomeric metallocene can be employed, since the cleavage of Si-Cp bond in each case results in the same product, irrespective of the stereoisomer employed.

This is particularly important for metallocenes in which Cp is an indenyl or tetrahydroindenyl radical, since the meso and rac form exist in the case of these ligands—irrespective of the further substitution pattern.

In the case of the compounds per se of the present invention, it is preferred that if $X^1$ is —Cl, $R^1$ and $R^2$ are —$CH_3$, each Cp is cyclopentadienyl, a is zero in each occurrence, and M is Zr, Ti or Hf, then $(X^2)_n$ is not $Cl_2$.

EXAMPLES

All the experiments were carried out under an inert gas with exclusion of oxygen and moisture.

Example 1

Preparation of [1-(chlorodimethylsilyl) tetrahydroindenyl] [tetrahydroindenyl]zirconium dichloride 2 g (4.4 mmol) of pure rac-dimethylsilylbis(tetrahydroindenyl)$ZrCl_2$ were dissolved in 50 ml of chloroform.

98 ml of gaseous, dry hydrogen chloride (4.4 mmol) were passed into this mixture at room temperature and dissolved.

The reaction mixture was stirred at room temperature, and the reaction was monitored by $^1$H-NMR spectroscopy.

When conversion was complete, all the solvent was removed, and the residue was recrystallized from hexane.

1.36 g (63% of theory) of pure product were isolated.

$^1$H-NMR (CDCl$_3$): 6.46 (d, 1H, H—Cp); 6.34 (t, 1H, H—Cp); 5.9 (d, 1H, H—Cp); 5.81 (t, 1H, H—Cp); 5.72 (t, 1H, H—Cp); 3.0–2.5 (m, 4H, H—C$_6$-ring); 1.95–1.55 (m, 4H, H—C$_6$-ring); 0.65 ppm (s, 3H, H$_3$C—Si); 0.62 ppm (s, 3H, H$_3$C—Si) Zr: (calc.: 18.5) found: 18.3 Cl: (calc.: 21.6) found: 21.3 Si: (calc.: 5.7) found: 5.9

Example 2

Example 1 was repeated; the gaseous hydrogen chloride was replaced by 4.4 ml of a one molar solution of dry hydrogen chloride in diethyl ether (4.4 mmol).

After work-up, 1.45 g of product (67% of theory) were isolated [$^1$H-NMR was identical to that in Example 1].

Example 3

1 g (2.2 mmol) of a 1:1 mixture of rac:meso-Me$_2$Si(tetrahydroindenyl)$_2$ZrCl$_2$ was dissolved in 100 ml of methylene chloride, and 2.2 ml of a one molar solution of dry hydrogen chloride in diethyl ether (2.2 mmol) were added at room temperature.

The reaction was again monitored by $^1$H-NMR.

The reaction product observed was again the formation of [(1-(chlorodimethylsilyl)tetrahydroindenyl)-(tetrahydroindenyl)]ZrCl$_2$.

0.77 g (71% of theory) of product was isolated [$^1$H-NMR was identical to that in Example 1].

Example 4

Example 2 was repeated. The Me$_2$Si(tetrahydroindenyl)$_2$ZrCl$_2$ was replaced by Me$_2$Si(tetrahydroindenyl)$_2$HfCl$_2$.

1.45 g (68% of theory) of [1-(chlorodimethylsilyl)tetrahydroindenyl ][tetrahydroindenyl]HfCl$_2$ were isolated.

$^1$H-NMR (CDCl$_3$): 6.38 (d, 1H, H—Cp); 6.24 (t, 1H, H—Cp); 5.8 (d, 1H, H—Cp); 5.71 (t, 1H, H—Cp); 5.64 (t, 1H, H—Cp); 3.1–2.5 (m, 4H, H—C$_6$-ring); 2.0–1.45 (m, 4H, H—C$_6$-ring); 0.64 ppm (s, 3H, H$_3$C—Si); 0.61 ppm (s, 3H, H$_3$C—Si)

Example 5

5 g of Me$_2$Si(tetrahydroindenyl)$_2$ZrCl$_2$, 250 ml of chloroform and 30 ml of one molar HCl in diethyl ether were stirred for 6 hours at 100° C. in a 2-liter pressure vessel. The investigation of a sample by $^1$H-NMR then showed complete conversion of the starting material.

After removal of the solvent and recrystallization, 3.2 g (59% of theory) of pure [1-(chlorodimethylsilyl)tetrahydroindenyl]][tetrahydroindenyl]ZrCl$_2$ were isolated.

What is claimed is:

1. A process for the preparation of an asymmetrically substituted compound of the general formula (1)

$$(R^1R^2X^1Si((R^3)_aCp))((R^4)_aCp)M(X^2)_n \qquad (1)$$

in which $R^1$ and $R^2$ are independently of one another the same or different and each is an alkyl radical containing 1 to 7 carbon atoms or an aryl radical containing up to 7 carbon atoms, $X^1$ is F, Cl, Br, I, p-tolylSO$_3$—, F$_3$CSO$_3$—, F$_3$CCO$_2$— or H$_3$CCO$_2$—, $R^3$ and $R^4$ are independently of one another the same or different and each is an alkyl or alkyl ether group containing 1 to 9 carbon atoms or an aryl or aryl ether group, containing up to 9 carbon atoms, and $0 \leq a \leq 4$ in each occurrence of a, Cp is a cyclopentadienyl, indenyl, tetrahydroindenyl or fluorenyl radical, M is a transition metal from any of groups 3–6 (IUPAC notation) of the Periodic Table, $X^2$ is F, Cl, Br or I, and n is the oxidation number of the transition metal minus 2, comprising reacting a compound of the general formula (2)

$$R^1R^2Si(Cp(R^3{}_a))(Cp(R^4{}_a))M(X^2)_n \quad (2)$$

where $R^1$, $R^2$, Cp, $R^3$, $R^4$, a, M, $X^2$ and n are as defined above, with an inorganic or organic acid $HX^1$ in an inert solvent, to effect selective cleavage of the Cp—Si bond, as shown in the general equation II $$R^1R^2Si(Cp(R^3{}_a))(Cp(R^4{}_a))M(X^2)_n + HX^1 \rightarrow$$
$$(R^1R^2X^1Si((R^3{}_a)Cp))((R^4{}_aCp)MX^2{}_n \quad (II).$$

2. A process according to claim 1, wherein the compound of formula (2) is reacted with one or more hydrohalic acids at 20°–100° C. in the presence of one or more halogenated hydrocarbons.

3. A process according to claim 1, wherein the compound of formula (2) is employed in the form of its rac:meso compounds.

4. A process according to claim 1, wherein M is Ti, Zr or Hf.

5. A compound of the general formula (1)

$$(R^1R^2X^1Si((R^3)_aCp))((R^4)_aCp)M(X^2)_n \quad (1)$$

in which $R^1$ and $R^2$ are independently of one another the same or different and each is an alkyl radical containing 1 to 7 carbon atoms or an aryl radical containing up to 7 carbon atoms, $X^1$ is F, Cl, Br, I, p-tolylSO$_3$—, F$_3$CSO$_3$—, F$_3$CCO$_2$— or H$_3$CCO$_2$—, $R^3$ and $R^4$ are independently of one another the same or different and each is an alkyl or alkyl ether group containing 1 to 9 carbon atoms or an aryl or aryl ether group containing up to 9 carbon atoms, and $0 \leq a \leq 4$, in each occurrence of a, Cp is a cyclopentadienyl, indenyl, tetrahydroindenyl or fluorenyl radical, M is a transition metal from any of groups 3-6 (IUPAC notation), of the periodic table, $X^2$ is F, Cl, Br or I, and n is the oxidation number of the transition metal minus 2, provided that if $X^1$ is —Cl, $R^1$ and $R^2$ are —CH$_3$, each Cp is cyclopentadienyl, a is zero in each occurrence, and M is Zr, Ti or Hf, then $(X^2)_n$ is not Cl$_2$.

6. A compound according to claim 5 of the general formula (1) in which Cp is the tetrahydroindenyl radical.

7. [1-(chlorodimethylsilyl)tetrahydroindenyl]-[tetrahydroindenyl]zirconium dichloride.

8. [1-(chlorodimethylsilyl)tetrahydroindenyl]-[tetrahydroindenyl]hafnium dichloride.

* * * * *

UNITED STATES PATENT AND TRADEMARK OFFICE
CERTIFICATE OF CORRECTION

PATENT NO. : 5,618,956
DATED : April 8, 1997
INVENTOR(S) : Richard Lisowsky

It is certified that error appears in the above-identified patent and that said Letters Patent is hereby corrected as shown below:

Column 4, line 64, Claim 1: "$X^z$" should read --$X^2$--

Signed and Sealed this

Thirtieth Day of June, 1998

Attest:

BRUCE LEHMAN

Attesting Officer     Commissioner of Patents and Trademarks